United States Patent [19]

Auroy et al.

[11] 4,119,645

[45] Oct. 10, 1978

[54] METHOD OF PREPARING PHTHALIC ANHYDRIDE

[75] Inventors: Michel Auroy; Maurice Goharel; Jacques Zoulalian, all of Chauny, France

[73] Assignee: Rhone-Progil, Paris, France

[21] Appl. No.: 817,139

[22] Filed: Jul. 20, 1977

Related U.S. Application Data

[63] Continuation-in-part of Ser. No. 460,176, Apr. 11, 1974, abandoned.

[30] Foreign Application Priority Data

Apr. 11, 1973 [FR] France .................................. 73 13072

[51] Int. Cl.$^2$ ............................................ C07D 307/89
[52] U.S. Cl. ............................. 260/346.4; 260/346.7
[58] Field of Search ............................ 260/346.4, 346.7

[56] References Cited

U.S. PATENT DOCUMENTS

| | | | |
|---|---|---|---|
| 2,512,283 | 6/1950 | Marotta et al. | 203/31 |
| 3,248,453 | 4/1966 | Beyrard | 260/346.4 X |
| 3,535,345 | 10/1970 | Egbert | 260/346.4 |
| 3,816,344 | 6/1974 | Shimizu et al. | 252/455 R |

FOREIGN PATENT DOCUMENTS 2,102,853  3/1972  France.

OTHER PUBLICATIONS

Process Technology, Reprint from Chemical Engineering, Mar. 4, 1974.

*Primary Examiner*—Richard L. Raymond

[57] ABSTRACT

A method for preparing phthalic anhydride by oxidation of o-xylene with air in which the reaction is self-sufficient in terms of energy and involves only low investment costs while providing a pure product in high yield in which the oxidation reaction is carried out in short tubes for minimum pressure drop over the reactor.

14 Claims, 2 Drawing Figures

METHOD OF PREPARING PHTHALIC ANHYDRIDE

This is a continuation-in-part of copending application Ser. No. 460,176, filed Apr. 11, 1974, now abandoned.

The invention relates to a method of preparing phthalic anhydride through oxidatin of orthoxylene by air.

It has long been possible to obtain phthalic anhydride by oxidation of o-xylene with air, over a catalyst comprising vanadium oxide, placed in nests of tubes in a reactor. The effluent gases from the oxidation reactors are passed into condensers and the condensate recovered is distilled to give relatively pure phthalic anhydride.

Oxidation releases a large amount of heat which is partially lost because the air used is greatly in excess of the xylene and because oxidation is carried out in very long tubes to obtain maximum conversion of the hydrocarbon. The latter results in a considerable pressure drop in the gases passing through the reactor, thus requiring large amounts of energy to compress the air fed to the reactor. Moreover, the amount of catalyst used is consequently large. The investment required, both to construct the apparatus and to purchase or prepare the catalyst, added to the unfavorable energy balance, detracts from the profitability of such conventional methods.

The problem of energy consumption is important to any industrial method. That problem has been recognized by the prior art. For example, U.S. Pat. No. 3,755,376 relates to a method for the preparation of phthalic anhydride by oxidation in vapor phase of an aromatic hydrocarbon with compressed air in a reaction zone at a pressure of at least 60 psig to produce a hot gaseous mixture containing the anhydride. The anhydride is then separated from the gaseous mixture by condensation, and a "fuel gas" and a gas containing molecular oxygen are mixed with the gas originating from the condensers for subsequent combustion to furnish energy to the air-compressing turbine used to feed the reaction zone.

The principal disadvantage of that type of method is that it requires an inflow of outside energy into the method in itself. Thus, it cannot be considered as entirely satisfactory because additional installations are required and the control of the combustion of exhaust gases constitutes an additional step. The heat from the reaction is not utilized to recover energy to improve the profitability of the process; in fact, this reaction heat is removed to assure the smooth operation of the oxidation reaction.

French Pat. No. 2,102,853, and its supplement 2,146,550, relate to a catalyst based on titanium and vanadium oxide deposited on an enamel-coated support which has excellent catalytic activity and mechanical strength, and to a method for the preparation of phthalic anhydride by oxidation in gaseous phase of orthoxylene which produces better yields and selectivities than the ones obtained by the preceding methods. The result of the operation at a low air/orthoxylene ratio is a gain in terms of compression energy. However, the method requires an intake of outside energy to feed the different steps which require energy.

The energy-requiring step is, in the preparation of phthalic anhydride, primarily the compression phase of the air entering the oxidation reactor. In fact, a high output of air is needed for the oxidation reaction, and thus it is necessary to be able to have available a high compression energy. This energy is furnished according to the methods of prior art, such as by an installation operating with electricity, for example. These energy-requiring steps are secondarily the heating stages (heating of the air, melting of the phthalic anhydride, etc.), the distillation phase and all the rotating machines (pumps, etc.).

It is an object of the present invention to provide a method for the preparation of phthalic anhydride which is autonomous in terms of energy consumed.

It is another object of the present invention to provide a method for the preparation of phthalic anhydride, which is autonomous in energy and which makes possible the production of a pure product at a high yield and high productivity.

It is another object of the invention to provide a method for the preparation of phthalic anhydride which is autonomous in energy and which makes possible the production, at a high yield and high productivity, of a very pure product without pollution of the environment.

The invention relates to a method for the preparation of phthalic anhydride by oxidation of orthoxylene with the aid of air in the presence of a catalyst containing vanadium and titanium oxide, followed by condensation, purification of the anhydride and treatment of the effluent gases. The air-orthoxylene mixture used has a weight ratio ranging between 18/1 and 24/1 with a low pressure loss in a plurality of tubes containing the catalyst, the heat released by the oxidation reaction being recovered in the form of high pressure steam by circulation of a heat-bearing fluid bath at a temperature ranging between about 360° and 400° C. about tubes containing the catalyst and by passage of the gaseous mixture originating from the tubes into a heat exchanger. The high pressure steam is used to make the entire method energy-autonomous.

This method is characterized in that oxidation is carried out in tubes with an internal diameter of 19 to 25 mm containing, over 1.20 to 2.20 m. grains of catalyst with an equivalent mean diameter of 4 to 8 mm, at a temperature of from 360 to 400° C., with an air:o-xylene weight ratio of 18:24 and an hourly discharge rate of the gaseous mixture of 3,600 to 6,900 g/h per liter of catalyst used; that the condensate is heated in the presence of sodium salts, and that all the effluent gases undergo post-combustion.

Catalysts used in the practice of this invention are known to the art, and are preferably those described in French Pat. No. 2,102,853 and in its addition No. 2146550 filed on July 19, 1971 in the name of "Produits Chimiques Pechiney-Saint-Gobain" under national registration No. 71 26278 and with the title "Catalysts for the oxidation of o-xylene to phthalic anhydride". These catalysts comprise a carrier, preferably of alumina, which is agglomerated in the form of pellets with a mean equivalent diameter of 4 to 8 mm by fritting or with cement, having a specific surface area of 0.04 to 0.4 $m^2/g$ and an internal porosity of 0.02 to 25 $cm^3$ per 100 g, and coated with a glaze which melts between 800 and 1200° C., comprising 20 to 60% by weight of $SiO_2$, 0 to 15% of $Al_2O_3$, 1 to 15% of $Na_2O$ and $K_2O$, 0.5 to 16% of alkaline earth metals and 0 to 40% of $B_2O_3$ (this last quantity preferably being from 20 to 40%). The glazed particle is covered with an active substance comprising 70 to 90% by weight of $TiO_2$ and a quantity of $V_2O_5$ representing 0.05 to 2% of the total weight of the particle of catalyst. The mean equivalent diameter is understood as being the diameter of the sphere which would have the mean volume of the particles.

The catalyst mass is placed in tubes of generally circular section, although a different section, e.g., a square one equivalent to a circle of 19 to 25 mm in diameter, may also be suitable. The mass is maintained in the tubes so that it does not provide any preferential paths or channeling for the gases over the length of 1.20 to 2.20 m which it occupies. A free length is left at the end of the tubes near the wall of the reactors.

A gaseous mixture of air and o-xylene, in a weight ratio of from 18 to 24:1, is passed through the catalyst at a rate of 3,000 to 6,900 g per hour per liter of catalyst.

The o-xylene may also contain a certain amount of impurities up to 5% of its weight.

Complete energy independence or self-sufficiency of the process can only be reached if a sufficient amount of heat is available and if this amount of heat is recovered satisfactorily. This must of course not be accomplished to the detriment of obtaining, with a high yield and a strong productivity, phthalic anhydride.

The problem of energy independence poses the problem of pressure loss throughout the installation, and more specifically through the reactor. The pressure loss, defined as energy to be supplied so that the gases will pass through the installation, must be low for, the higher it is the more energy must be available to compress the air.

In spite of the small dimension of the grains of catalyst (in fact, the smaller the diameter of the grains, the higher the load loss) and due in part to the short length of the reactive zone of the reactor tubes (in fact, the longer the tube the higher the heat loss), the heat loss is low and a pressure drop of 0.4 to 0.5 kg/cm² over the reactor. The diameter of the tubes according to the invention permits good heat exchange with the heat-bearing fluid (for example, a mixture of sodium nitrite and nitrate and/or potassium nitrite and nitrate, both in melted condition) circulating between a boiler and the reactor.

The temperature in the reactor is maintained by circulating a bath of dissolved salt (a mixture of sodium and/or potassium nitrate and nitrite). The bath is heated when an operation is being started up, but when normal working conditions are reached a large amount of heat is recovered by keeping the bath at 360° to 400° C. in the reactors. The heat recovered, together with the heat of the gaseous mixture emerging from the reactors (and, optionally, the heat from the post-combustion reaction of the effluent gases) in the form of steam entirely or partially at high pressure (40 to 100 bars), makes the process independent as far as energy is concerned, apart from the starting up period.

On leaving the reactor, the gases have a temperature of over 360° C.; this temperature cannot be lower than that of the salt bath. They are passed into a heat exchanger which recovers part of their thermal energy, and their temperature drops to a few degrees (about 5° C.) above the condensation temperature of the phthalic anhydride.

Because of the small flow of gas, the condensers into which the gases and vapors are then directed are smaller than those in conventional installations. The fluid circulating in the condensers is 2° to 6° C. above the dew point of the water conveyed with the gases. In the method of the invention, the dew point depends less on the hygrometric state of the air than it does in conventional processes.

Thereafter, the anhydride undergoes a first distillation enabling light impurities including benzoic acid to be separated at the top. In a second distillation process, the virtually pure phthalic anhydride is separated at the top of the column used. The pressures in the two successive columns are preferably kept at from 400 to 760 mm/Hg and from 60 to 100 mm/Hg respectively.

The gaseous effluents are drawn off at the outlets from the condensers, the aging vessel and the columns then sent through a layer of catalyst, generally 15 to 60 cm thick and made up of particles of palladium-based alumina of an equivalent diameter of 4 to 6 mm; the proportion of palladium relative to the total weight of palladium is 0.1 to 0.6%. Complete combustion of the effluents starts from 190° C. (the temperature at which the gases are introduced through the catalytic layer).

The low rate of gases at the inlet is 36,000 to 9,000 l/h per liter of catalyst.

The combustion gases, which no longer contain any carbon monoxide, leave the post-combustion enclosure at a temperature over 300° C., and, if desired, can be directed to a heat exchanger in which their thermal energy can be recovered before the gaseous mixture, having been made non-toxic, is discharged into the atmosphere.

Apart from the various advantages of the method which have been brought out above, it should be noted that the total loss of phthalic anhydride is of the order of 1.5%, versus about 0.6% in the condensers, about 0.6% in the distillations and about 0.2% carried away by the residues. Furthermore, the non-recovered anhydride, like the non-oxidized xylene and the various oxidizable compounds which form in the installation, can be, if desired, partially exploited in post-combustion, in the form of thermal energy which can be recovered as an additional source of energy, over and above the energy recovered from the oxidation reaction. Thus, the energy which can be, if desired, recovered from the post-combustion gases, serves as an optional source of further energy. The energy recovered from the oxidation reaction alone is sufficient to render the process self-sufficient from the energy standpoint.

The invention will now be described in greater detail by reference to the appended drawings.

Figure 1:
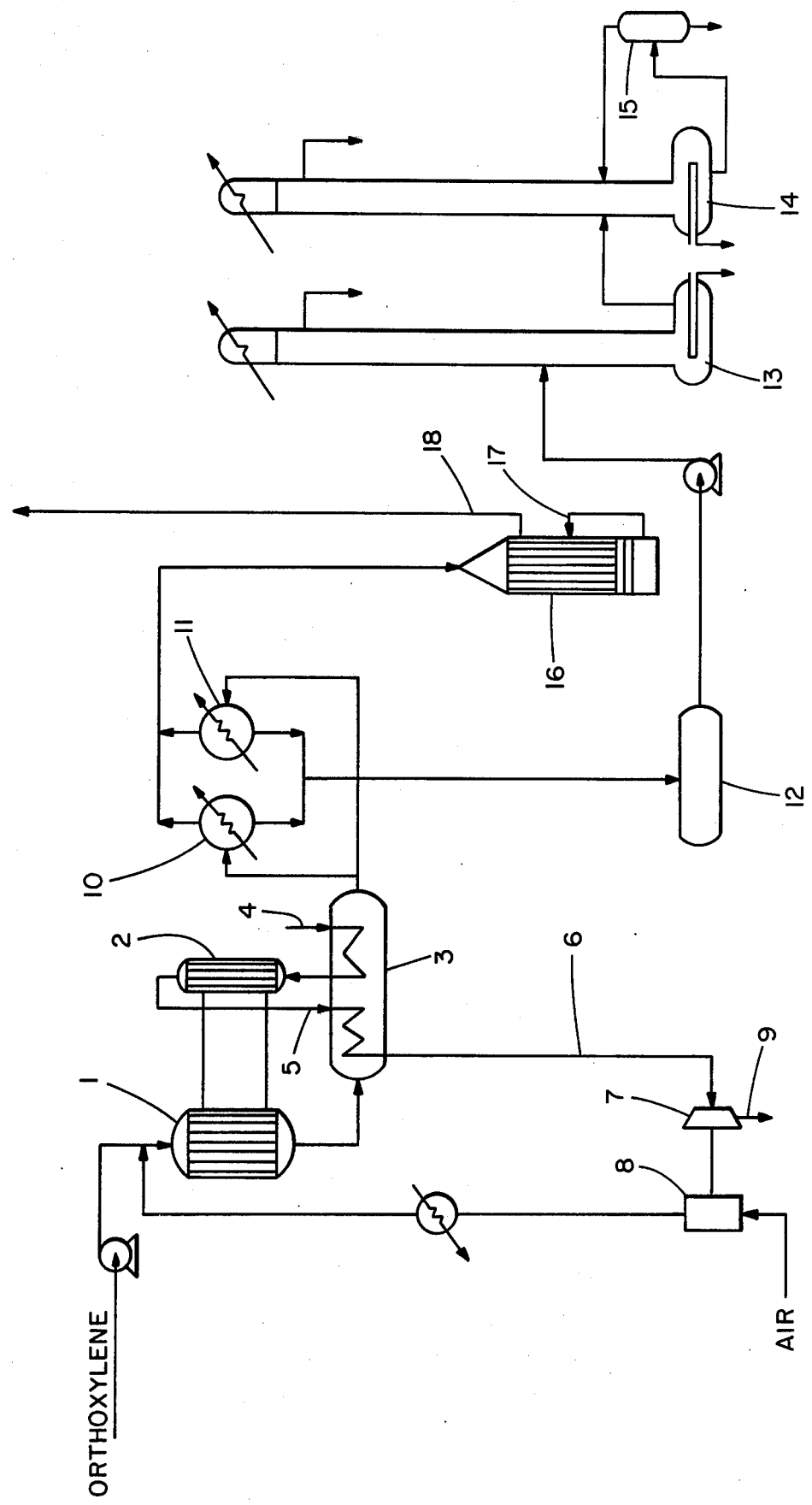
FIG. 1 shows the case where independence in energy is attained without using the heat released by the catalytic combustion of the gaseous effluents.

Air and orthoxylene are introduced in mixed state into the reactor 1, constituted by a plurality of tubes containing the catalyst. The reaction heat is eliminated by circulation of the heat-bearing fluid between the reactor 1 and the boiler 2.

The gaseous mixture originating from the reactor 1 which is at a temperature exceeding 360° C. passes through the heat exchanger 3 into which at 4 a jet of water penetrates which passes through the boiler 2 which generates the saturated high pressure steam (pressure: 40–100 bars) which again penetrates at 5 the exchanger 3 where it is superheated; the steam obtained feeding at 6 the turbine 7 at a pressure ranging from 40 to 100 bars and a temperature near that of the heat-bearing fluid. This turbine operates the compressor 3 to compress the air for the oxidation. The additional available steam at 9 directly or indirectly feeds (by turbo alternator for example) all the other steps of the process which require energy.

The gases originating from the exchanger 3 are then directed toward the condensation phase. According to one conventional method, one (or several) condenser(s) [10] is (are) used for the condensation of the phthalic anhydride in solid form while another one (or several) [11] which is outside the circuit is heated until the condensate melts.

Other devices like the one permitting the condensation on solid granulated supports described in U.S. Pat. No. 3,952,022 could likewise be used under the method of the invention. The crude melted anhydride is directed into the storage vat 12. Then the anhydride is subjected to a first distillation in column 13 which alloys for the separation at the head of the slight impurities among which benzoic acid is found. In a second distillation, performed in column 14, the pure phthalic anhydride is separated at the column head. The pressures in both successive columns are maintained preferably between 400 and 760 mm Hg and 60 to 100 mm/Hg, respectively. For the quality of the product recovered at the column head, it is advantageous to submit the melted crude anhydride originating fromm 12, prior to the entry into column 13, to a heat treatment. The anhydride is heated to a temperature ranging from 240° to 290° C. for 3 to 9 hours. It also is advantageous to continuously remove a certain quantity at the foot of the vat of the second column and to subject it at 15 to a thin layer evaporation at a pressure of 60 to 300 mm Hg. The evaporated fraction, rich in phthalic anhydride is recycled in the distiller of the column, while the heavy residues may be treated, as described in U.S. Pat. No. 3,923,839, in order to obtain granulates whose elimination cannot cause air or water pollution.

The gaseous effluents of the condensers, and possibly the light by-products originating from the distillation columns are subjected at 16 to a catalytic combustion. They are dispatched over a layer having generally a thickness of 15 to 60 cm of a catalyst constituted from grains 4 to 6 mm in equivalent diameter of palladiumized alumine; the ratio of palladium being 0.1 to 0.6%.

A complete combustion of the effluents is primed from 190° on (a temperature at which the gases are introduced through the catalytic layer).

The yield of the gases at the input is 36,000 to 9,000 liters/hour per liter of catalyst. The combustion gases no longer contain carbon monoxide and are reintroduced there so that this combustion is autonomous in itself on the energy level.

They are discharged at 18 and can be ejected into the atmosphere without any danger to the environment.

Figure 2:
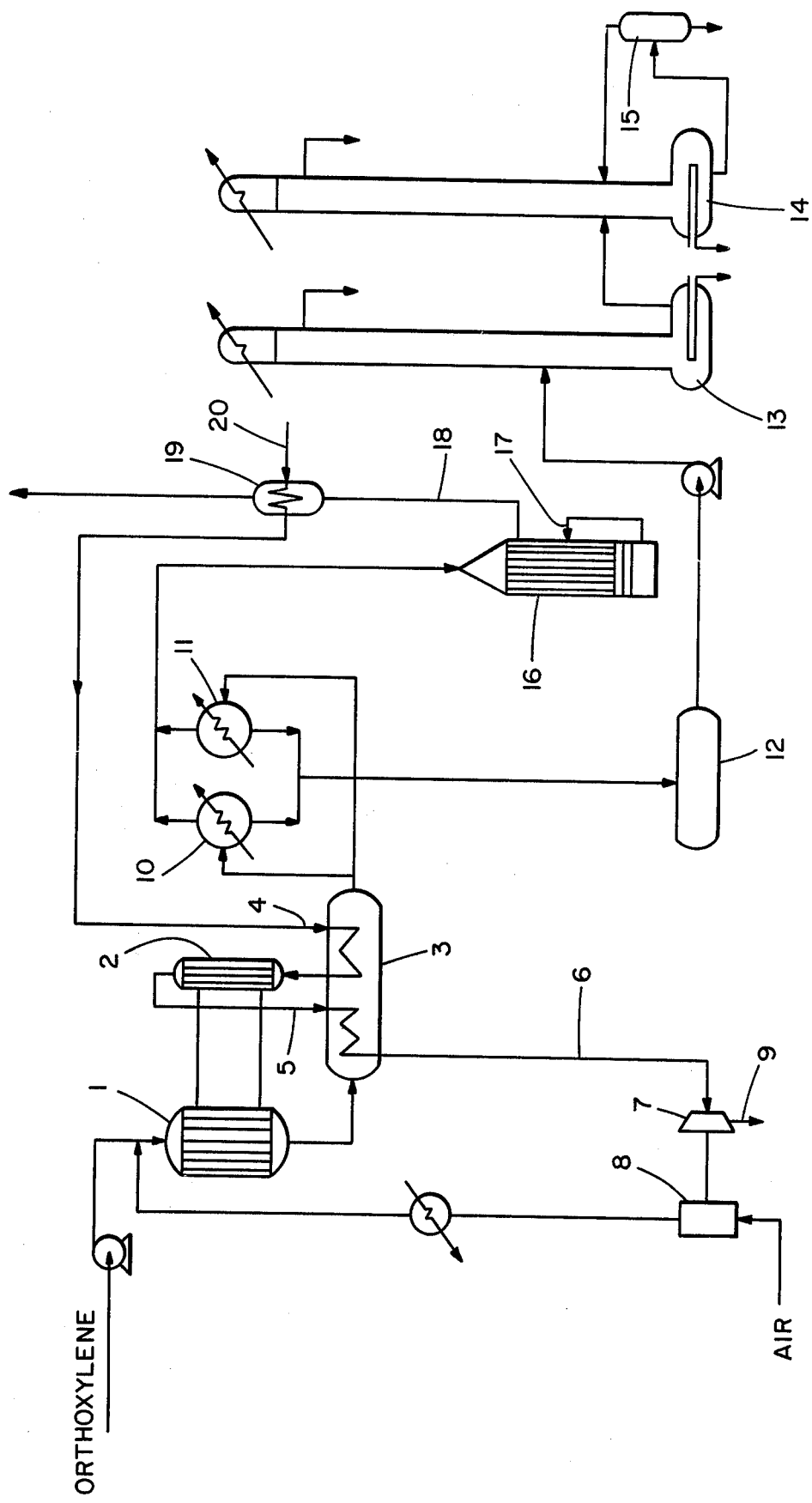
FIG. 2 represents the case where this released heat is used.

Prior to their ejection into the atmosphere they may (FIG. 2) pass through a heat exchanger 19. This heat exchanger may then be used to heat the water jet which eventually is introduced into the exchanger 3 at 4.

Besides the important advantages of these methods which have been evidenced above, it should be noted that the total loss in phthalic anhydride is on the order of 1.5% that is about 0.6% in the conderser, 0.6% in the distillation and about 0.2% carried along by the residues. Moreover, this unrecovered anhydride, like the unoxidized orthoxylene and the different oxidizable components forming in the installation, is utilized in the catalytic combustion in the form of heat energy.

Having described the basic concepts of the invention, reference is now made to the following examples which are provided by way of illustration, and not of limitation, of the practice of the invention.

EXAMPLE 1

A mixture of air and o-xylene (99% by weight) in a weight ratio of 22, pre-heated to 135° C. and under a relative pressure of 441 mm/Hg, is sent at the rate of 6,300 g per liter of catalyst per hour into a reactor comprisng 4,650 tubes with an internal diameter of 21 mm and a total length of 1.50 m, containing pellets of catalyst of an equivalent diameter of 4 to 7 mm over a length of 1.35 m. The catalyst carrier comprises electrically molten alumina which has been crushed then agglomerated into pellets in a granualator with the aid of a cement. The porosity of the carrier is 25 ml/100 g, the mean diameter of the pores being from 80 to 100 microns, and the specific surface area is from 0.2 to 0.3 $m^2g$. Every liter of carrier is coated with 150 g of glaze comprising 49.9% by weight of $SiO_2$, 7.7% of $Al_2O_3$, 1.2% of $Na_2O$, 0.4% of $K_2O$, 11.5% of CaO and 29.3% of $B_2O_3$, the glaze being deposited from a suspension of these compounds in water than baked for 2 hours at 960° C. The active substance is deposited on the glazed carrier in a rotating drum in a confined atomosphere, in 2 hours at 430° C. To every liter of carrier there is used 16 g of ammonium hexavanadate in 500 $cm^3$ of water, to which are added 10 g of urea dissolved in 60 $cm^3$ of water and 75 g of anatase in suspension in water containing 1 $cm^3$ of ethanolamine.

The temperature of the molten bath (sodium nitrite and sodium nitrate circulating between reactor 1 and boiler 2) in which the catalysis tubes are located is kept at 372° C.

The weight yield of the oxidation process is 104% relative to xylene.

The effluent gases from the reactor, at a temperature of 370° to 372° C., pass through the heat exchanger 3 in which they are cooled to 155° C. Then they are passed to the condensers.

Condensation takes place in the stationary condensers comprising tubes with vanes within which a heat-carrying fluid circulates at a temperature of 55° to 65° C. during the condensation phase. When a condenser is sufficiently filled with anhydride it is isolated from the reactor and the fluid is then heated to 160° C., causing the anhydride deposited in the condensers which have been cut off from the reactor to melt.

The product is passed into an agitated vat containing 3,800 kg of crude anhydride and a mixture of 0.25 kg of $CO_3Na_2$ and 0.35 kg of $NO_3Na$. The mean dwell time in the vat is 6 hours at 280° C.

The product is withdrawn after this treatment and directed to a first column in which the pressure is from 500 to 600 mm/Hg. 72 kg of light fraction are eliminated per hour. The heavy fraction is let into the shaft of a second column 14 with a pressure of 70 to 90 mm/Hg at the top.

Substantially pure (99.7%) phthalic anhydride is recovered at the top. 13 kg/h from the bottom of the vat of that column is passed into a thin-layer evaporator with an active surface of 0.5 $m^2$. A rotor with blades, turning at a speed of 12 revs/sec., spreads out this layer with an average thickness of 5 mm. The temperature of the wall is 275° C. and the absolute pressure in the evaporator is 200 mm/Hg. Anhydride is thus evaporated and recycled into the boiler of the second column. The residues are granulated and solidified by spraying 2 $m^3/h$ of water at ambient temperature onto the stream flowing out through a tube with an internal diameter of 32 mm and are deposited in a vat containing 2 m³ of water, from which they are eliminated. A cylindrical skirt which dips 10 cm into the water, which is connected to the outflow tube by a cone and which has the 5 spray nozzles inside it, prevents any corrosive vapors from being given off.

The weight of residues is 4.75 kg/h and the anhydride content (by weight) is 20%.

The total weight yield of recovered phthalic anhydride is 102.6%.

The gases and vapors emerging from the condensers, the ageing vat (not shown) and the columns are sent at the rate of 10,500 m³/h (measured at normal temperature and pressure) at a temperature of 210° C. into a post-combustion reactor containing 0.3 m³ of catalyst with 0.3% of palladium deposited on microporous alumina at a thickness of 20 cm. In the catalytic bed the temperature of 260° C. near the inlet rises commensurately with the advance of the gases, which are sent at 390°-400° C. into a heat exchanger for pre-heating the intake gases and super-heating the water which will subsequently provide high pressure steam. The cooled gases do not contain any detectable carbon monoxide when they are discharged into the atmosphere.

The gases from the catalyst bed, at a temperature of 200° C., pass through the heat exchange 19 where they preheat the water jet 20 from 100° to 130° C. That water jet then passes through the heat exchanger 3 to supply water to the boiler 2 at 254° C. The saturated steam originated from boiler 2 is at a pressure of 43 bars.

After further heat at 5, the steam in line 6 is at a pressure of 40 bars and a temperature of 365° C.

About one-third of this steam can be used for the steam consumption of the process (i.e., degasification of the water jet 20, pre-heating of the air entering the reactor 1, melting of the phthalic anhydride in the condensers, etc.). The remaining steam can be passed through a turbo alternator to produce the electric power necessary for the compression of air entering the reactor 1.

EXAMPLE 2

A mixture of air and o-xylene (99.1% by weight) is introduced at 135° C. into a reactor comprising 13,260 tubes of an internal diameter of 21 mm, containing the catalyst described in the previous example over a length of 2 m.

The temperature is also set at 377° C. in the salt bath surrounding the tubes.

The subsequent treatments are similar to those in the previous example.

In a first test the weight ratio of air to o-xylene is 22:1 and the flow rate of orthoxylene is 210 g/h per liter of catalytic mass. The weight yield in respect of o-xylene is 105.2% and the total yield is 103.2%.

In a second test the weight ratio of air to o-xylene is 20:1 and the flow rate of orthoxylene is 240 g/h per liter of catalytic mass. The weight yield in respect to o-xylene is 104.1% and the total yield is 102.7%.

EXAMPLE 3

This example relates to an autonomous method in energy not using the energy released by the catalytic post-combustion reaction (FIG. 1). A mixture of air and orthoxylene, preheated to 144° C. is introduced at a weight ratio of 22 at the rate of 210 grams/hour of orthoxylene per liter of catalyst into one or several reactors 1 containing a total of 32,000 tubes of 21 mm i.d. and including over a length of 2 meters catalyst balls of 5.2 mm ± 0.5 mm in diameter. This catalyst is constituted from titanium and vanadium oxides deposited on a support formed from fritted clay. The oxidation yield is 108, that is to say 108 kilograms of crude anhydride are obtained for 100 kilograms 100% orthoxylene.

The reaction heat to be eliminated again at the level of the reactor 1 is recovered in the boiler 2 and in an exchanger not shown which is used to heat the thermofluid used for the distillation. This latter exchanger, connected in parallel with boiler 2 is fed at a constant output. The temperature of the sodium nitrite-nitrate salt bath is 365° C. The stages of condensation, heat treatment, catalytic combustion are conducted like in example 1. The effluent gases from the catalytic combustion are not used to attain energy independence, and thus are discarded directly into the atmosphere at a temperature of 208° C.

Energy independence is obtained by using the heat released by the oxidation reaction of orthoxylene on the one hand at the level of the salt bath and on the other hand at the level of the effluent gases originating from the oxidation reactor. 27 tons/hour (t/h) of water enter at 4 at a temperature of 265° C. at 55 bars. At 626.4 tons/hour of super-heated steam are obtained at 340° C. and 52 bars. The steam feeds a backpressure turbine at 11 bars. 10.6 tons/hour of this steam are used for the shop's steam requirements (thermal degasification of the water entering the exchanger at 4, heating the air entering the oxidation reactor, melting of the phthalic anhydride in the condensers, piloting the circuits and storages), the remainder is dispatched into a turbo alternator which generates 1700 KW/hour, used in the facility.

EXAMPLE 4

This example relates to a process not using the energy released by the post-combustion reaction to attain energy independence.

The operation is carried out like in example 3. 10.6 tons/hour of the steam obtained in 6 (26.4 tons/hour) are used for the shop's steam requirements. 15.8 tons/hour feed a turbo alternator which makes it possible to generate about 2400 KW/hour, of which 1500 KW/hour are needed for the compression of air, the remainder for the shop's needs. The back pressure of the compressor is 0.55 bars. The hourly output of the air compressor is 100,000 kilograms.

It will be understood that various changes and modifications can be made in the details of formulation and procedure without departing from the spirit of the invention, especially as defined in the following claims.

We claim:

1. In a process for the preparation of phthalic anhydride by oxidation of ortho-xylene with air in the presence of an oxidizing catalyst in an exothermic reaction wherein the reaction gases issue at elevated temperature, circulating a heat exchange fluid through the reaction zone to maintain reaction temperature within said zone and to recover heat of reaction, recovering the heat of reaction from said heat exchange fluid and recovering heat from the reaction gases by passing said heat exchange fluid and said hot reaction gases in heat exchange with water at a temperature whereby the reaction gases issue from the heat exchange at a temperature at least 5° C. above the condensation temperature of phthalic anhydride to provide steam utilized in carrying out the process.

2. The process as claimed in claim 1, in which the temperature in the reaction zone is maintained at about 360°–400° C.

3. The process as claimed in claim 2 in which the temperature of the reaction gases exhausted from the reaction zone is within the range of about 360°–400° C.

4. The process as claimed in claim 1, in which the reaction is carried out in the reaction zone by passage of the mixture of air and ortho-xylene through tubular zones containing the oxidation catalyst.

5. The process according to claim 4 wherein the air-orthoxylene mixture is passed into a plurality of tubular zones containing the catalyst with an hourly output ranging between 3000 and 6900 grams/liter of catalyst.

6. The process according to claim 4 wherein the air-orthoxylene mixture is passed into a plurality of tubular zones containing the catalyst having an inner diameter ranging between 19 and 25 mm.

7. The process according to claim 4 wherein the air-orthoxylene mixture is passed into a plurality of tubular zones containing the catalyst in the form of balls having an equivalent average diameter ranging between 4 and 8 mm.

8. The process according to claim 7 wherein the variation of the diameters of said balls is less than 10%.

9. The process according to claim 4 wherein the air-orthoxylene mixture is passed into a plurality of tubular zones containing the catalyst over a length ranging between 1.20 and 2.20 meters.

10. A process according to claim 4 wherein the heat exchange fluid is maintained at a temperature ranging from 360° to 400° C.

11. A process according to claim 4 wherein the catalyst contains vanadium and titanium oxides.

12. The process as claimed in claim 1 which includes the steps of cooling the reaction gases to condense phthalic anhydride, leaving a gaseous effluent, and subjecting the condensed phthalic anhydride to purification by distillation with the removal of impurities and combustible by-products, and subjecting the combustible by-products from the distillation and the said gaseous effluent from the condensation to combustion, and recovering the heat of combustion.

13. The process as claimed in claim 12, in which the recovered heat of combustion is added to the water to produce steam at high pressure.

14. The process as claimed in claim 12, in which the recovered heat of combustion is used to preheat the air utilized in the oxidation reaction of the ortho-xylene.

* * * * *